(12) United States Patent
Gupta et al.

(10) Patent No.: US 9,619,213 B2
(45) Date of Patent: Apr. 11, 2017

(54) MOBILE MEDICAL APPLICATIONS WITH SEPARATED COMMUNICATION AND DEVELOPMENT ENVIRONMENT FOR THE SAME

(71) Applicants: Sandeep Gupta, Phoenix, AZ (US); Ayan Banerjee, Tempe, AZ (US)

(72) Inventors: Sandeep Gupta, Phoenix, AZ (US); Ayan Banerjee, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 14/694,152

(22) Filed: Apr. 23, 2015

(65) Prior Publication Data
US 2015/0309773 A1    Oct. 29, 2015

Related U.S. Application Data

(60) Provisional application No. 61/983,053, filed on Apr. 23, 2014.

(51) Int. Cl.
*G06F 9/44*    (2006.01)
*G06F 9/45*    (2006.01)
*G06Q 50/22*   (2012.01)

(52) U.S. Cl.
CPC .............. *G06F 8/36* (2013.01); *G06F 8/447* (2013.01); *G06Q 50/22* (2013.01)

(58) Field of Classification Search
CPC ............ G06F 8/36; G06F 8/447; G06Q 50/22
USPC .................................................. 717/106–109
See application file for complete search history.

(56) References Cited

U.S. PATENT DOCUMENTS

| | | | |
|---|---|---|---|
| 8,255,280 B1 | 8/2012 | Kay et al. | |
| 8,886,316 B1* | 11/2014 | Juels | A61N 1/37252 607/30 |
| 2012/0030046 A1 | 2/2012 | Fullerton | |
| 2013/0060574 A1 | 3/2013 | Perlman et al. | |
| 2013/0066650 A1 | 3/2013 | Ackerman et al. | |
| 2013/0232082 A1* | 9/2013 | Krawczewicz | G06F 19/323 705/55 |
| 2013/0238360 A1 | 9/2013 | Bhathal | |
| 2013/0263260 A1 | 10/2013 | Mahaffey et al. | |
| 2013/0317377 A1 | 11/2013 | Gupta et al. | |

(Continued)

OTHER PUBLICATIONS

Sorber et al, "An Amulet for Trustworthy Wearable mHealth", 2012, ACM, 6 pages.*

(Continued)

*Primary Examiner* — Ted T Vo
(74) *Attorney, Agent, or Firm* — Michael Best & Friedrich LLP

(57) ABSTRACT

Systems and methods are provided for a mobile medical application operating environment and automated/semi-automated systems for creating application software for the operating environment. In the operating environment, all data storage and communication with external devices relating to sensitive medical data and operations is handled by a data manager application concurrently running with the medical application on a mobile device. Multiple medical applications can be run concurrently on the mobile device with reduced risk of data failure, thereby simplifying the design and release process for mobile medical applications.

19 Claims, 4 Drawing Sheets

(56) References Cited

U.S. PATENT DOCUMENTS

2015/0164432 A1 6/2015 Gupta et al.
2015/0304101 A1 10/2015 Gupta et al.

OTHER PUBLICATIONS

Petersen et al., "Experience Report: Functional Programming of mHealth Applications", 2013, ACM, 6 pages.*
Pradeep Chakraborty, "Amulet's GUI design tool enables Smartphone-like graphics in 8-, 16-, and 32-bit embedded systems", 2010, PC's Semiconductors Blog, retrieved from http://pcsemicon.blogspot.com/2010/04/amuletsguidesigntoolenables.html , 1 page.*
N. Agrawal et al., "Mobile Data Sync in a Blink", HotStorage'13 Proceedings of the 5th USENIX conference on Hot Topics in Storage and File Systems, 2013.
K.E. Andersen et al., "A Bayesian Approach to Bergman's Minimal Model", In C.M. Bishop, B.J. Frey (Eds.), Proc. of the 9th International Workshop on Artificial Intelligence, 2003.
P. Bagade et al., "Safety Assurance of Medical Cyber-Physical Systems using Hybrid Automata: A Case Study on Analgesic Infusion Pump", In Proceedings of the 4th Medical Cyber-Physical Sstems Workshop (MCPS'13), Philadelphia, USA, 2013.
P. Bagade et al., "Protect your bsn: No handshakes, just namaste!" In 2013 IEEE International Conference on Body Sensor Networks (BSN), pp. 1-6, 2013.
P. Bagade et al., "A holistic tool for developing a wireless home-based health monitoring system", Biomedical Instrumentation & Technology, 47(s1), pp. 64-71, 2013.
A. Banerjee et al., "Challenges of implementing cyber-physical security solutions in body area networks", In BodyNets '09: Proceedings of International Conference on Body Area Networks, 2009.
A. Banerjee et al., "Ensuring safety, security, and sustainability of mission-critical cyber-physical systems", Proceedings of the IEEE, 100(1), pp. 283-299, 2012.
A. Banerjee et al., "Health-dev: Model based development pervasive health monitoring systems". In 2012 Ninth International Conference on Wearable and Implantable Body Sensor Networks (BSN), pp. 85-90, 2012.
A. Banerjee et al., "Your mobility can be injurious to your health: Analyzing pervasive health monitoring systems under dynamic context changes", In 2012 IEEE International Conference on Pervasive Computing and communications (PerCom), pp. 39-47, 2012.
A. Banerjee et al., "Spatio-temporal hybrid automata for safe cyber-physical systems: A medical case study", In 2013 ACM/IEEE International Conference on Cyber-Physical Systems (ICCPS), pp. 71-80, 2013.
A. Banerjee et al., "PEES: physiology-based end-to-end security for mHealth", In Proceedings of the 4th Conference on Wireless Health, 2013.
A. Banerjee et al., "Tackling new frontiers in modeling and analysis of cyber-physical systems", In 1 st workshop on Cyber-Physical Systems Education, 2013.
A. Banerjee et al., "BAND-AiDe: A Tool for Cyber-Physical Oriented Analysis and Design of Body Area Networks and Devices", ACM Trans. on Embedded Computing Systems, Special issue on Wireless Health Systems, 2010.
A. Banerjee et al., "Using Formal Methods to Improve Home-Use Medical Device Safety", Biomedical Instrumentation & Technology: Home Healthcare, vol. 47, No. s1, pp. 43-48, 2013.
P.L. Dolan, "Health app certification program halted" http://exclusive.multibriefs.com/content/health-app-certification-program-halted, published Dec. 17, 2013, downloaded on Jan. 25, 2016.
S.K.S. Gupta et al., "Criticality Aware Access Control Model for Pervasive Applications". High-Confidence Automotive Cyber-Physical Systems, Fourth Annual IEEE International Conference on Pervasive Computing and Communications (PerCom 2006), pp. 257-2006.
S.K.S. Gupta, "Towards formal framework for modeling and evaluation of high-confidence criticality-aware software for distributed cps: A white paper", National Workshop for research on High Confidence Transportation Cyber Physical Systems: Automotive, Avaition, and Rail, 2008.
S.K.S. Gupta, "Towards human-centric middleware for future automotive cps: A white paper", High-Confidence Automotive Cyber-Physical Systems, 2008.
S.K.S. Gupta et al., "GDCSim: A Tool for Analyzing Green Data Center Design and Resource Management Techniques", 2011 International Green Computing Conference and Workshops (IGCC), pp. 1-8, 2011.
S.K.S. Gupta et al., "GDCSim—A Simulator for Green Data Center Design and Analysis", ACM Transactions on Modeling and Computer Simulation, vol. 24, Iss. 1, 2014.
T. Hardjono et al., "Towards a trustworthy digital infrastructure for core identities and personal data stores", The Global Forum on Identity, 2013.
P. Hui et al., "Human mobility models and opportunistic communications system design", Philosophical Transactions of the Royal Society A: Mathematical, Physical and Engineering Sciences, 366(1872), pp. 2005-2016, 2008.
E. Mikk et al., "Hierarchical automata as model for statecharts", In Proc. of the Asian Computing Science Conference (ASIAN'97), vol. 1345 of LNCS. Springer-Verlag, 1997.
P.E. McSharry et al., "A dynamical model for generating synthetic electrocardiogram signals", IEEE Transactions on Biomedical Engineering, 50(3), pp. 289-294, 2003.
J. Milazzo et al., "bHealthy: A Physiological Feedback-based Mobile Wellness Application Suite", Proceedings of the 4th Conference on Wireless Health, 2013.
T. Mukherjee et al., "A modeling framework for evaluating effectiveness of smart-infrastructure crises management systems", In IEEE Conference on Technologies for Homeland Security, 2008 (HST), pp. 549-554, May 2008.
T. Mukherjee et al., "Performance modeling of critical event management for ubiquitous computing applications". In MSWiM '06: Proceedings of the 9th ACM international symposium on Modeling analysis and simulation of wireless and mobile systems, pp. 12-19, 2006.
T. Mukherjee et al., "CRET: A crisis response evaluation tool to improve crisis preparedness", IEEE International Conference on Technologies for Homeland Security (HST'09), May 2009.
T. Mukherjee et al., "MCMA+CRET: A mixed criticality management architecture for maximizing mission efficacy and tool for expediting certification of uavs", IEEE International Workshop on Mixed Criticality: Roadmap to Evolving UAV Certification at the Cyber-Physical Systems Week, Apr. 2009.
S. Nabar et al., "GeM-REM: Generative Model-driven Resource Efficient ECG Monitoring in Body Sensor Networks", In 2011 International Conference on Body Sensor Networks (BSN), pp. 1-6, 2011.
S. Nabar et al., "Evaluation of Body Sensor Network Platforms: A Design Space and Benchmarking Analysis", In Wireless Health 2010, WH '10, pp. 118-127, 2010.
P. Valensi et al., "Influence of blood glucose on heart rate and cardiac autonomic function. The DESIR study", Diabetic Medicine, 28(4), pp. 440-449, 2011.
Y. Prakash et al., "Energy efficient source coding and modulation for wireless applications.", In Proceedings of the IEEE Wireless Communications and Networking Conference (WCNC 2013), pp. 212-217, Mar. 2003.
S.K.S. Gupta et al., "Towards a Propagation Model for Wireless Biomedical Applications", IEEE International Conference on Communications ICC'03, pp. 1993-1997, 2003.
T.R. Rossiter et al., "A Comparison of EEG Biofeedback and Psychostimulants in Treating Attention Deficit Hyperactivity Disorders", Journal of Neurotherapy, Summer, pp. 48-59, 1995.
L. Schwiebert et al., "Research challenges in wireless net-works of biomedical sensors", In MobiCom '01: Proceedings of the 7th annual international conference on Mobile computing and networking, pp. 151-165, 2001.

(56) References Cited

OTHER PUBLICATIONS

J. Sproston et al., "Simulation and Bisimulation for Probabilistic Timed Automata", In FORMATS, pp. 213-227, 2010.

Q. Tang et al., "BER Performance Analysis of an On-off Keying based Minimum Energy Coding for Energy constrained Wireless Sensor Applications", 2005 IEEE International Conference on Communications, ICC 2005, pp. 2734-2738, 2005.

Q. Tang et al., "Communication Scheduling to Minimize Thermal Effects of Implanted Biosensor Networks in Homogeneous Tissue", IEEE Transactions on Biomedical Engineering, vol. 52, No. 7, pp. 1285-1294, 2005.

K.K. Venkatasubramanian et al., "Green and Sustainable Cyber-Physical Security Solutions for Body Area Networks", In BSN '09: Proceedings of the 2009 Sixth International Workshop on Wearable and Implantable Body Sensor Networks, pp. 240-245, 2009.

K.K. Venkatasubramanian et al., "EKG-based key agreement in body sensor networks", IEEE INFOCOM Computer Communications Workshops, pp. 1-6, 2008.

K.K. Venkatasubramanian et al., "PSKA: Usable and Secure Key Agreement Scheme for Body Area Network", IEEE Transactions on Information Technology in Biomedicine, vol. 14, No. 1, pp. 60-68, 2010.

K.K. Venkatasubramanian et al., "Physiological Value Based Efficient Usable Security Solutions for Body Sensor Networks", ACM Transactions on Sensor Networks (TOSN), vol. 6 Issue 4, 2010.

K.K. Venkatasubramanian et al., "Plethysmogram-based secure inter-sensor communication in body area networks", Military Communications Conference, MILCOM 2008, pp. 1-7, 2008.

J. Milazzo et al., "Sharing is Caring: A Data Exchange Framework for Co-Located Mobile Apps", Fourth International conference on Computational Science, Engineering and Information Technology (CCSEIT 2014), Pune, India, Aug. 2014.

C.K. Hsieh et al., "Performance Evaluation of Android IPC for Continuous Sensing Applications", downloaded from http://www.hotmobile.org/2012/papers/dandp/Performance_Evaluation_of_Android_IPC.pdf on Jan. 25, 2016.

T. Gu et al., "A middleware for building context-aware mobile services", in 2004 IEEE 59th Vehicular Technology Conference, 2004. VTC 2004—Spring., vol. 5., pp. 2656-2660, 2004.

B.-G. Chun et al., "Mobius: unified messaging and data serving for mobile apps", in Proceedings of the 10th International conference on Mobile systems, applications, and services, pp. 141-154, 2012.

\* cited by examiner

MOBILE MEDICAL APPLICATIONS WITH SEPARATED COMMUNICATION AND DEVELOPMENT ENVIRONMENT FOR THE SAME

RELATED APPLICATIONS

This application claims the benefit of U.S. Provisional Application No. 61/983,053, filed on Apr. 23, 2014 and entitled "TRUSTWORTHY MOBILE MEDICAL APPLICATION MODEL AND DEVELOPMENT ENVIRONMENT," the entire contents of which are incorporated herein by reference.

STATEMENT REGARDING FEDERALLY SPONSORED RESEARCH OR DEVELOPMENT

This invention was made with government support under grants 1116385 and 1231590 awarded by the National Science Foundation. The government has certain rights in the invention.

BACKGROUND

The present invention relates to medical applications for mobile devices. In particular, the present invention relates to development platforms, architecture framework, and safety/security of mobile medical applications.

SUMMARY

According industry reports, by 2018, 1.7 billion smartphone users will have downloaded at least one health application. Such widespread adoption of smartphone-based medical apps will open new avenues for innovation, bringing mobile medical apps (MMAs) to the forefront of low cost healthcare delivery. A smartphone user may have multiple "apps" running on a smart phone or tablet controlling his health in a collaborative manner and sharing data. Such applications might range from simple data monitoring to more complex actuation control for devices such as, for example, infusion pumps.

Mobile medical apps (MMAs) work closely with human physiology through sensing and control. As such, it is essential for them to achieve intended functionality without having harmful effects on human physiology or compromising the privacy of health data in spite of runtime faults caused, for example, by service availability and application coding errors. Key challenges in ensuring correct functioning of MMAs include maintaining privacy of health data, long-term operation of wearable sensors, and ensuring that no physical harm is done to a user by the MMAs. Providing evidence of such safety, security, and sustainability (S3) properties can increase development time and may require higher skill sets for the developer. As such, although ensuring S3 is essential, it often acts as a hindrance to innovation.

Various embodiments described herein provide a tool for partially automating the process of developing and optimizing code for medical health applications. In some embodiments, the system receives a high-level description of the functionality of the health app (for example, expressed in Architectural Analysis and Description Language (AADL) format) and outputs security enabled code for interfacing with sensors, storing data, and communicating data to other apps, other devices, or remote storage systems (e.g., a cloud-based EHR management environment). In some embodiments, the system will also apply static analysis tools to test the automated code for errors. Furthermore, for apps that control actuation devices in a closed loop, the system will allow developers to test their generated apps for patient safety using algorithms such as, for example, non-linear spatio-temporal hybrid automata.

In some embodiments, medical device applications running on a user device (e.g., a smart phone or tablet) will be configured to interface with sensors, external devices, other apps, and remote storage systems only through a medical data manager application or "Trustworthy Data Manager" (TDM). The TDM application is optimized and tested to provide secure and reliable communication and safe operation of the mobile app regardless of user errors and varying operating conditions. As a result operation of app-controlled medical devices and storage of medical data is less susceptible to app coding errors or run-time fault conditions.

In one embodiment, the invention provides a method of developing a mobile medical software application. A code development system receives specification information defining operational characteristics of a first mobile medical software application. The code development system then automatically generates a data manager software application. The generated data manager includes portions of previously written software code stored on a non-transitory computer-readable memory of the code development system. These previously written software code are experimentally verified to satisfy safety and security criteria. The portions of previously written software code are selected and arranged by the code development system such that the generated data manager software application is configured to communicate with the first mobile medical software application and to provide communication with other software applications and one or more external devices based on the specification information received for the first mobile medical software application. The first mobile medical software application is generated such that the first mobile medical software application is configured to communicate with the data manager software application and is not capable of direct communication with any external device.

In another embodiment, the invention provides a mobile medical system comprising a first external medical device, a second external medical device, and a mobile device. The mobile device includes a processor and a non-transitory memory storing instructions that, when executed by the processor, operate a plurality of software applications including a first mobile medical software application, a second mobile medical software application, and a mobile medical data manager software application. Operating the mobile medical data manager includes providing all communication between the first mobile medical software application, the second mobile medical software application, the first external medical device, and the second external medical device. Operating the first mobile medical software application and the second mobile medical software application includes performing a data operation related to a medical function and communicating with the mobile medical data manager to transfer data related to the data operation to or from the external medical devices. Neither the first mobile medical software application, nor the second mobile medical software application is capable of communicating directly with any external device—all communications to and from the mobile medical software applications are provided through the mobile medical data manager.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
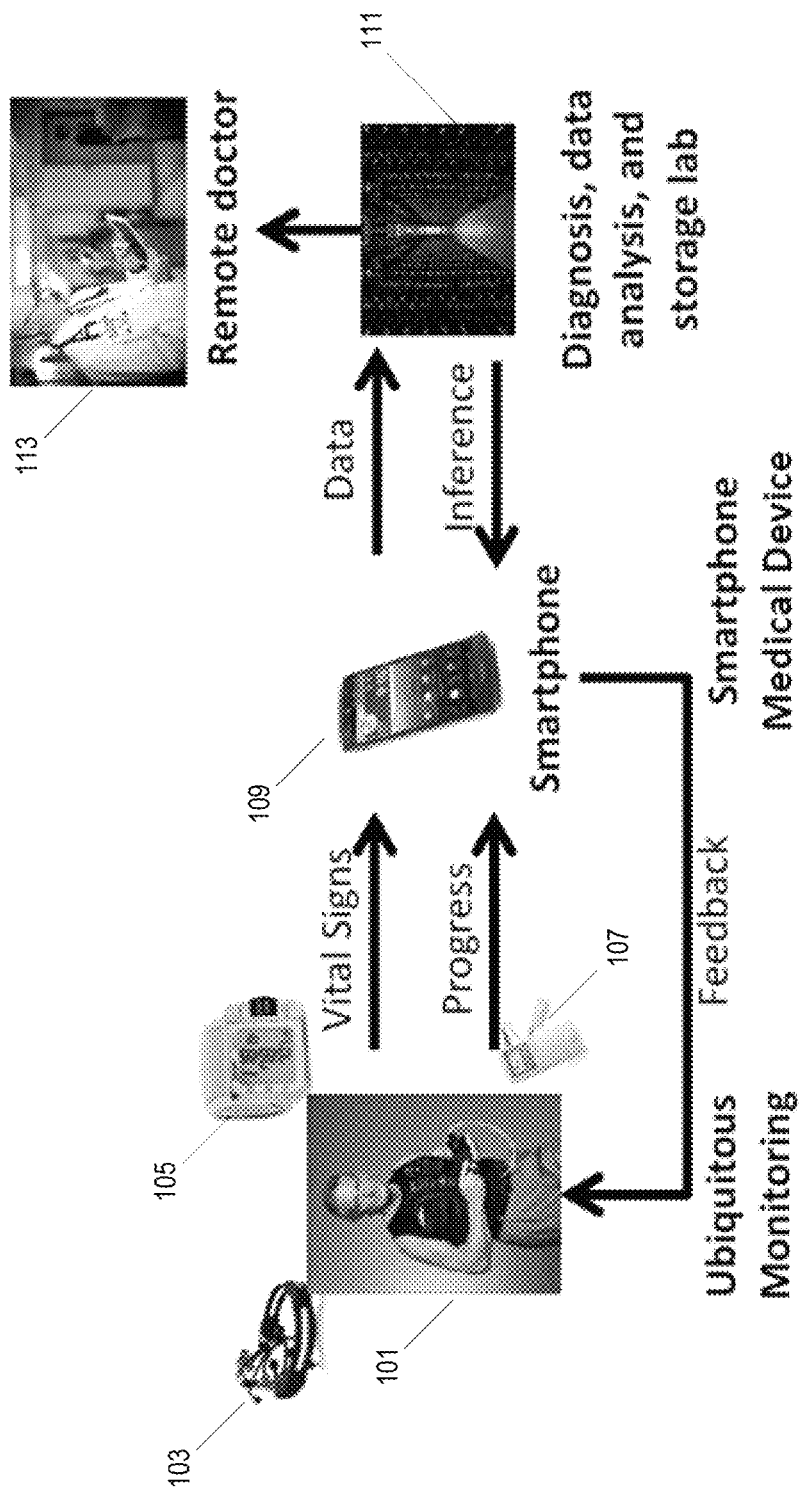
FIG. 1 is a block diagram of an example of smartphone-based suite of medical functionality provided by mobile medical applications (MMAs) according to one embodiment.

FIG. 1 illustrates an example of a communication network for a user 101 utilizing multiple mobile medical applications (MMAs). The user 101 may be prescribed a specific medical device or sensor 103 or may utilize their own non-prescription device such as, for example, a blood pressure monitor 105 or a step-counter/activity monitor 107. In this example, each device collects data about the user 101 including, for example, vital signs and activity progress, and transmits the data to a smartphone 109 running one or more MMAs. The smartphone 109 may then forward the data to a remote system 111 for diagnosis, analysis, and/or storage. For example, the remote system 111 may be a medical record repository server or a cloud-based storage environment. A medical professional (e.g., a doctor) can then access the data and other diagnostic information through another device 113 such as, for example, a desktop computer, a smartphone, or a tablet.

Diagnostic and analysis data, which may be generated manually by the medical professional 113 or automatically by the remote system 111, can then be transmitted back to the smartphone 109 where it can be utilized by the user 101 or the connected sensor/actuator devices 103, 105, 107. For example, in some MMAs, the user 101 will monitor a graphical user interface displayed on the smartphone 109 which provides feedback regarding a medical condition or progress towards a goal (e.g., a step-counter). In other MMAs, the smartphone 109 may transmit a signal to a device or actuator to modify the operation of the device based on feedback. For example, one MMA may operate as an "artificial pancreas" that receives sensor data, processes that data, and transmits an operating instruction to a communicatively coupled insulin infusion pump associated with the user 101.

In MMAs, like those illustrated in the example of FIG. 1, a wearable sensor can collect physiological data and communicate it to the smartphone 109 through a wireless channel. The smartphone 109 in turn can communicate the data to a cloud server 111 where it can be stored in an electronic health record (EHR). As noted above, the smartphone 109 can also control safety critical devices such as a drug infusion pump. In this way, the control outputs computed by the MMA can directly affect the physiology and well-being of the user 101. In such cases, the control algorithms must be verified for patient safety. In fact, because some MMAs operating on smartphones are considered to be "medical devices" by the FDA, documentation of such testing and verification may be required before the MMA can be made available to the public.

Due to lack of in-depth knowledge about human physiology, smartphone app developers might fail to consider these safety concerns. Further, since the smartphone is not a dedicated healthcare platform, non-medical apps such as games, might affect system performance and data reliability (e.g., via rapid battery depletion), thereby the availability and operation of the medical app. Also, all communications between the sensors, the smartphone 109, and the cloud 111 take place through the wireless channel which may be susceptible to security attacks.

Figure 2:
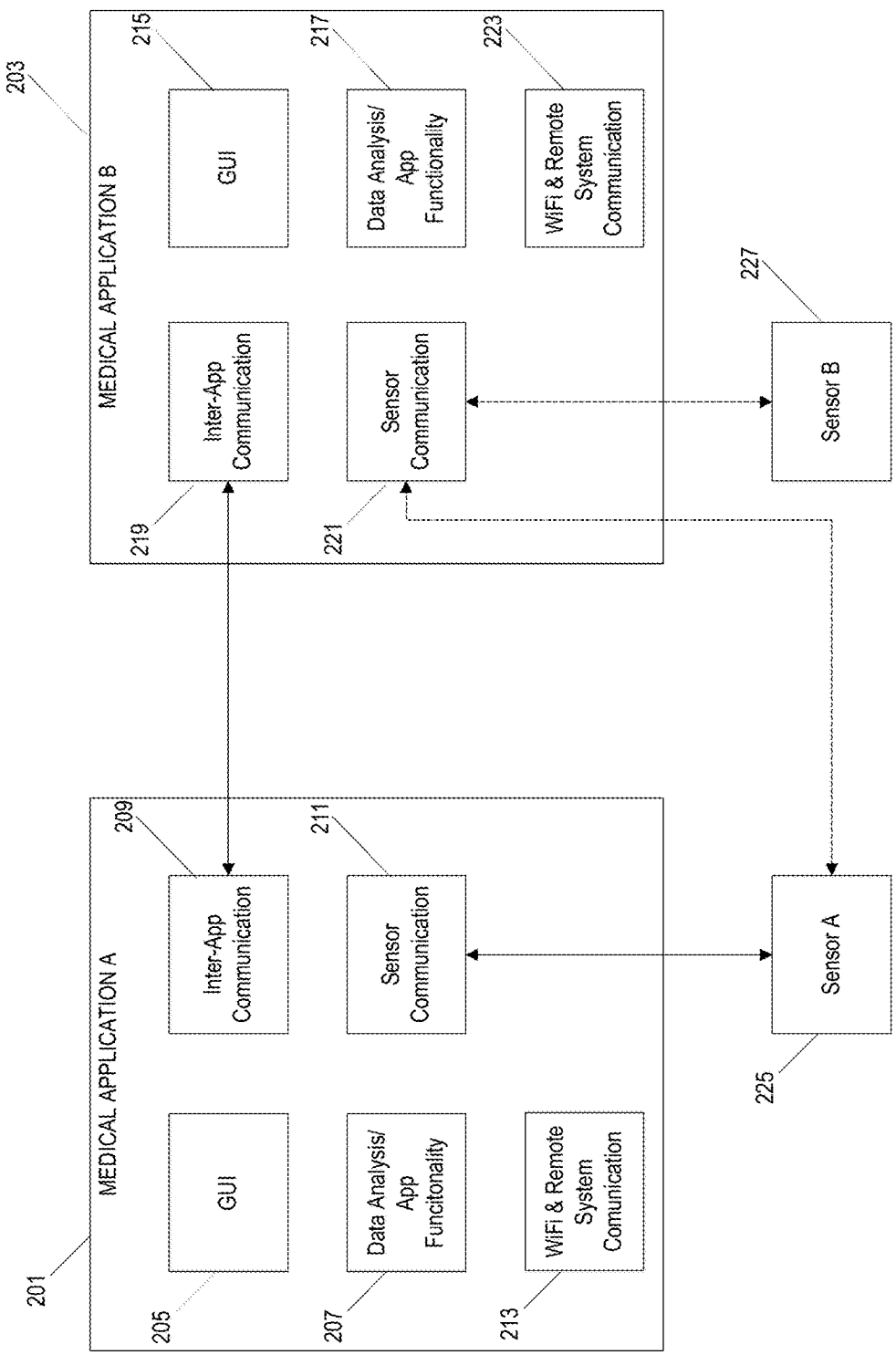
FIG. 2 is a block diagram of a first example of a mobile medical application architecture for the system of FIG. 1.

FIG. 2 illustrates one example of a software architecture model for mobile medical applications that addresses the reliability and security concerns noted above on an app-by-app basis. The user in this example is operating two medical applications—Medical Application A 201 and Medical Application B 203—on the same smart phone. Medical Application A 201 includes a graphical user interface 205, a module controlling the data analysis and other substantive application functionality 207, a module to control and facilitate communication with other applications running on the same smartphone (i.e., inter-app communication module 209), a module for managing communication between the application and a communicative coupled sensor (sensor communication module 211), and a module for managing communication via Wi-Fi with other devices and remote systems (module 213).

Similarly, Medical Application B 203 also includes its own graphical user interface 215 and a module for controlling the data analysis and other substantive functionality of the app (i.e., module 217). Furthermore, Medical Application B 203 must also include modules for managing and regulating communication with other apps operating on the same smartphone (module 219), with any communicative coupled sensors (module 221), and with other devices or remote systems via Wi-Fi (module 223).

This framework creates system redundancies in the modules of Medical Application A 201 and Medical Application B 203. For example, each developer must design and implement code to control the interactions between the smartphone, the specific app, and the external sensors. This may be a somewhat acceptable design characteristic when the first application 201 is utilizing one sensor 225 and the second application 203 is using a different sensor 227. However, in situations where both applications 201, 203 are utilizing data from the same sensor 225, the redundant sensor communication modules 211, 221 increase the load on system resources and may affect the reliability of the sensor 225.

Furthermore, although there are synergistic benefits to providing for communication and data sharing between two medical applications 201, 203 running on the same smartphone, making each application responsible for implementing its own inter-app communication requires some degree of knowledge about the input-output characteristics of other applications in order to effective implement communication and data sharing between apps.

Lastly, because the FDA now regulates certain MMAs as medical devices, the system functionality and communication interface modules of each app must separately undergo extensive testing, validation, and documentation. These added requirements may dissuade app developers from designing and releasing MMAs that could otherwise be beneficial to specific patients or to the public at large.

Figure 3:
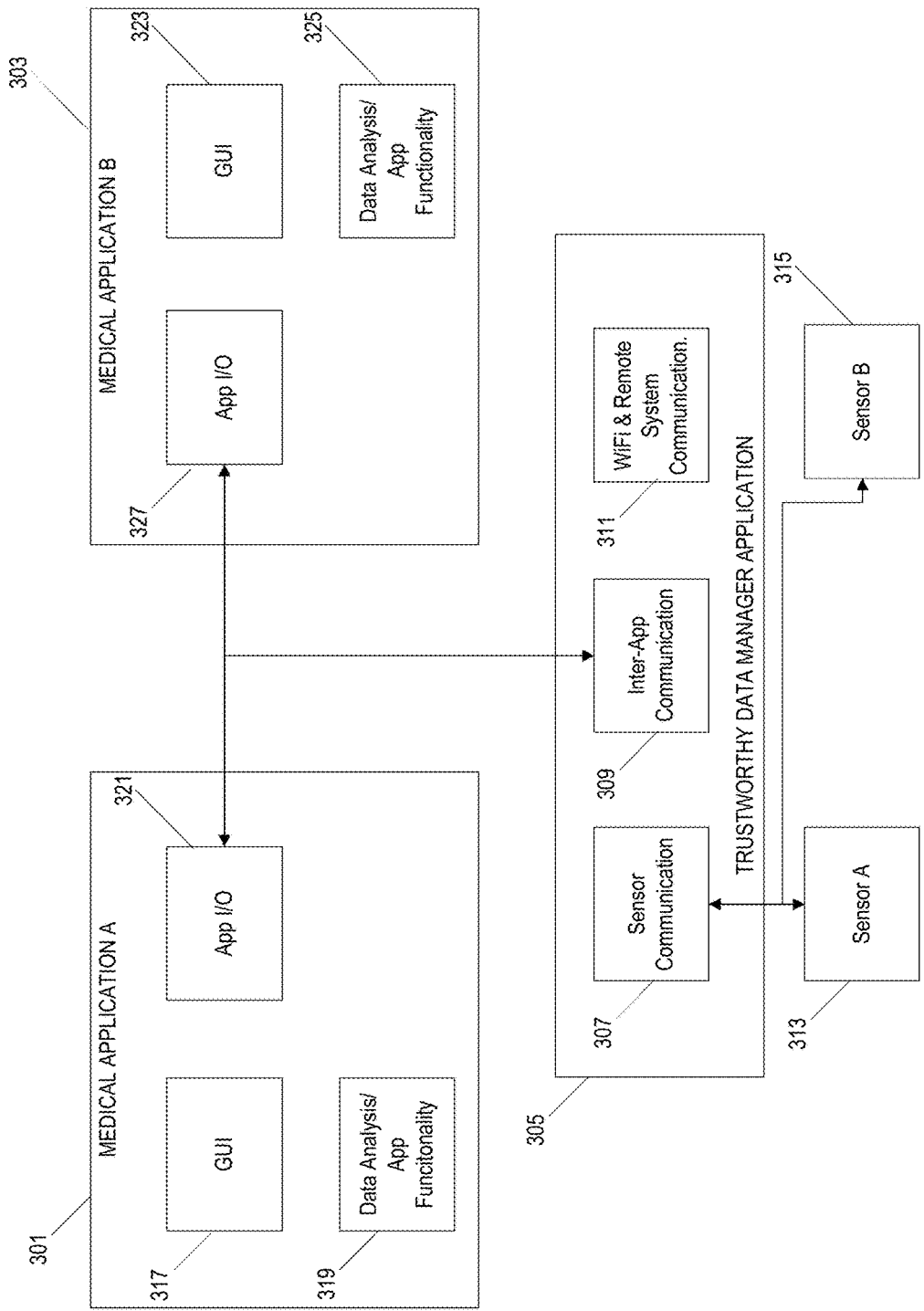
FIG. 3 is a block diagram of a second example of a mobile medical application architecture for the system of FIG. 1 using a trustworthy data manager application.

FIG. 3 illustrates an alternative software architecture framework that may enable objective evaluation of S3 requirements (i.e., safety, sustainability, and security) and provide a trustworthy operating environment for sensitive operations such as actuator control, sensor interface, sensor code, and cloud communication. Furthermore, by using a standard model that allows multiple MMAs to operate as a "suite," automated tools such as hybrid automata-based model checking techniques can be used to evaluate patient safety due to interactions between human physiology and application software. Sensor software design can also be optimized to obtain sustainable design for long-term availability. Moreover, security enabled software for interfacing the smartphone with sensors, actuators, and remote services (e.g., cloud environments) can be generated through partially automated processes.

In the architectural framework of FIG. 3, the MMA sensor/actuator interfaces, data communication, and data storage mechanisms are isolated from the core mobile device GUI and processing algorithms. In the example of FIG. 3, two mobile medical applications are being run on the same smartphone: Medical Application A 301 and Medical Application B 303. Furthermore, a third application 305 (i.e., the Trustworthy Data Manager (TDM) Application) is also being run on the same smart phone to handle internal and external communications, including, for example, communications between the two applications 301, 303 and communication with the external sensors 313, 315.

The content and complexity of each individual MMA is greatly simplified under this framework. The first application 301 includes a GUI 317, the functional processing algorithms specific to the first application (module 319), and a basic application I/O module 321. Similarly, the second application 303 includes a GUI 323, the functional processing algorithms 325, and another basic application I/O module 327. The I/O module 321, 327 of each application does not need to be capable of comprehensive internal and external communication. Instead, in some implementations, the I/O module simply needs to control a fixed number of memory locations where output data generated by the application is to be stored and to access memory locations where input data from the TDM application 305 can be found.

Notably, in the framework illustrated in FIG. 3, each MMA does not need to provide its own secure, sustainable, and safe data communication modules. Instead, a separate application—the TDM 305—provides optimized code for communication with external sensors (module 307), for communication between applications running on the same smartphone (module 309), and for communications with other external devices and remote systems via Wi-Fi (module 311).

In the framework of FIG. 3, the MMA software itself (i.e., Medical Application A 301 or Medical Application B 303) is in charge of only the graphical and algorithmic aspects of the application. Every instance of data communication to the sensor, cloud, data storage in the smartphone, control inputs to the actuator, and other interaction with the user is performed through the TDM application 305. This framework enables development of MMAs in the form of a suite, where participating apps are certified by the regulatory agencies for safety, sustainability, and security. The app model registry may provide guidelines to other apps to become part of the application suite (e.g., the types of sensors being used by currently available apps in the application suite, sensor sampling frequency, energy management algorithms, etc.).

However, to allow new MMAs to be developed that are not restricted by compliance with the existing guidelines of a specific application suite, a new TDM 305 can be developed and implemented that modifies the requirements and guideline—effectively creating a new group of MMAs (or application suite).

The application model of FIG. 3 ensures that S3 properties are taken into account during new MMA development. Any form of control input from an MMA is safety assured by checking it with a hybrid automata based model, as discussed in further detail below. Any sensor communicating with the TDM 305 supports long term availability with sustainable design. Finally, any form of data communication is privacy ensured by the TDM. Also, data collected by different applications are kept in secured databases shared only with certified applications (similar in principal to application sandboxing).

Furthermore, the architectural framework illustrated in FIG. 3 can be implemented by a semi-automated application development system that ensures safety from interactions, sustainability in sensor usage, and security of data (i.e., the S3 principles). The semi-automated application development can also generate a customized TDM application 305 for interfacing with specific sensors and other data communication. In various implementations, a developer can use the development tool to either (a) verify that a previously developed MMA satisfies trustworthiness requirements and/or (b) automatically generate critical parts of the code that will sufficiently address S3 vulnerabilities.

The (semi)automated application development tool can be a implemented as a software application running, for example, on a desktop computer, laptop computer, or tablet computer. In other words, the system would include a processor and a non-transitory computer-readable memory storing instructions that, when executed by the processor, provide the application development functionality. In other embodiments, the development tool is implemented as a web- or network-based design environment where use input is entered through a user-end terminal (e.g., a personal computer with Internet/network access) and forwarded to a remote server system that provides the development tool functionality as described below.

Figure 4:
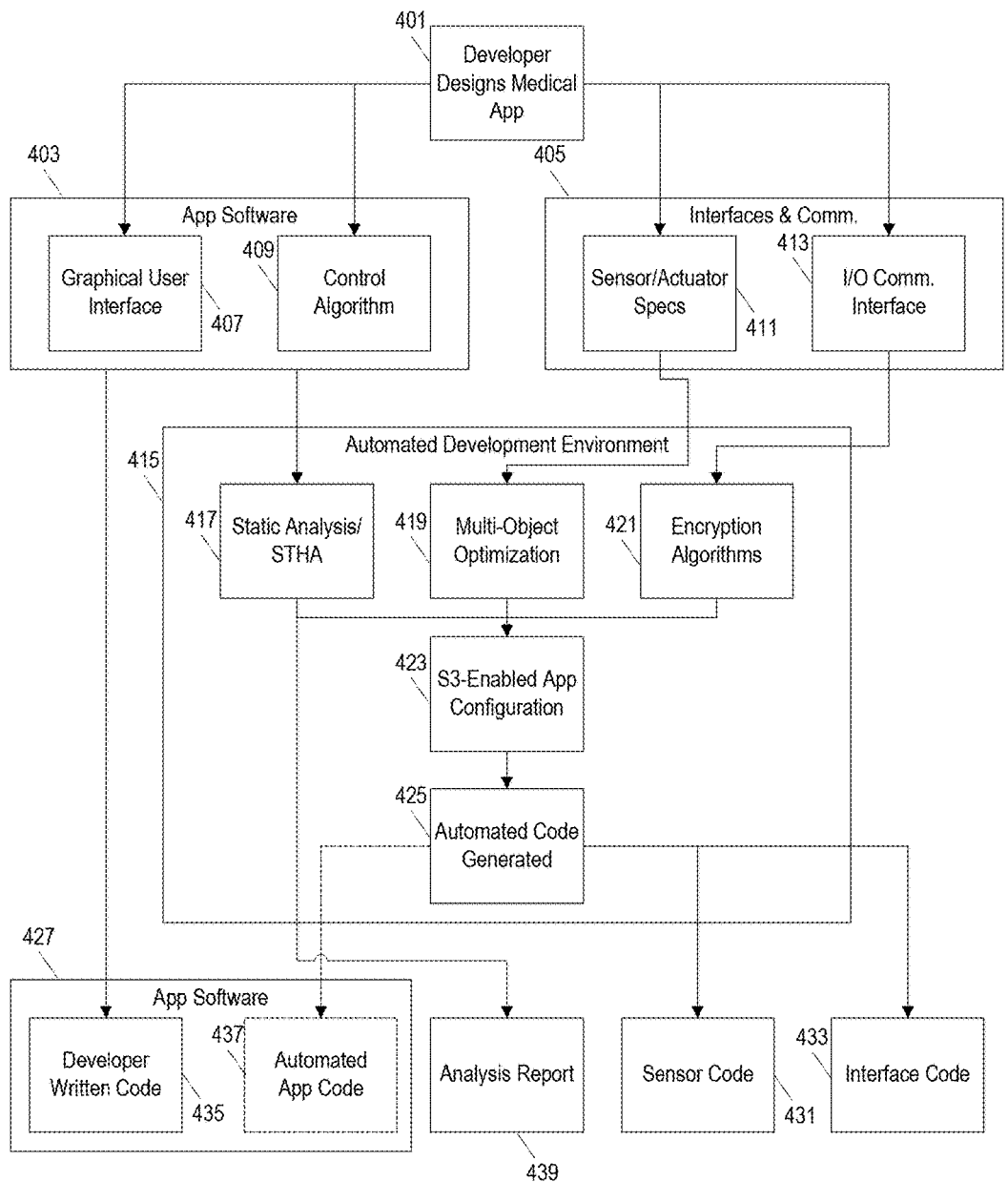
FIG. 4 is a flowchart of a partially-automated method of developing mobile medical applications according to the architecture of FIG. 3.

FIG. 4 illustrates one example of a method implemented by the application development tool to assist a developer in creating a S3-verified MMA. The software developer begins by providing a high-level design of his app as input to the system (step 401). The high-level specification may be provided and formatted according to a system-specific modeling language or may utilize a standard modeling format such as, for example, Architectural Analysis and Description Language (AADL). AADL is an accepted industry standard format and is generic enough to describe computational methods of smartphone aps as well as physiological aspects of the human body.

The "design" specification provided by the software developer includes an "app software" component 403 and an "interfaces and communication" component 405. The "app software" component 403 defines the graphical user interface 407 and the control algorithm 409 for the MMA. The "interfaces and communication" component 405 defines specifications 411 for interacting with certain sensors and actuators that are to be utilized by the MMA and other I/O communication interface protocol 413). Both the application software component 403 and the interfaces and communication component 405 are provided as inputs to the automated development environment (ADE) 415. The ADE 415 performs static analysis of the application software (step 417) using, for example, spatio-temporal hypbrid automata, as described in further detail below. The ADE 415 analyzes the sensor/actuator specifications 411 and performs a multi-object optimization routine 419 to optimize how sensors and actuators can be monitored and controlled to optimize performance variables such as, for example, execution time, energy consumption, etc. The ADE 415 also generates appropriate encryption algorithms according to the I/O communication interface specification 413 provided by the developer (step 421). Based on the output of the static analysis of the application-specific component (step 417), the multi-object optimization (step 419), and the developed encryption algorithms (step 421), the ADE 415 configures the application according to S3 principles and constraints (step 423).

Based on the output of the application configuration step 423, the ADE 415 outputs automatically generated code modules (step 425) that conform to the operational requirements specified by the developer and to the S3 principles (or other performance verification standards). These code modules can be assembled using pre-written code that is optimized and adjusted based on the output of the analysis and configuration performed by the ADE 415.

The output of the process illustrated in FIG. 4 is an application software component 427 (i.e., the MMA), sensor code 431, and code 429 configured to manage interfaces and communication. In the example of FIG. 4, application code written by the developer (portion 435) is combined with automated code 437 generated by the ADE 415 to form the MMA 427. The TDM 429 in this example is, however, generated entirely by automated code provided by the ADE 415 and includes optimized communication code 433 (including data encryption algorithms and code for communicating with external sensors and actuators). The sensor code 431 output by the ADE 415 can be uploaded to the specific external sensors to control sensor-side functionality and communications with the smartphone. The ADE 415 also outputs an analysis report 439 describing the results of the static analysis performed on the MMA design. This report 439 can then be used to document application safety, for example, for FDA review or certification for inclusion in an application suite or medical application marketplace.

Although, in the example of FIG. 4, the MMA code includes a combination of developer written code 427 and automatically generated code 437, the degree to which the resulting MMA utilizes automated code can vary in different implementations or can be controlled by developer preferences. For example, in some situations, a developer may choose to manually create the code for the graphical user interface and the control algorithm of the MMA and to use automatically generated code from the ADE 415 only for I/O interface with the TDM. In other situations, a developer may prefer to have the ADE 415 develop all of the code of the MMA without using any developer written code.

Furthermore, the sensor and smartphone code generated by the ADE 415 can then also be passed through a static analyzer to validate the code against data type and memory related errors. The static analyzer, the STHA reachability analysis, sustainable optimized sensor design, and the security primitives are then used to generate the certification report 439 stating the findings and conclusions of the ADE 415. The output code and the certification report can then be reviewed by expert personnel in the field to certify the application. If the MMA fails certification, then the developer can redesign and again use the ADE 415 according to FIG. 4. IN some implementations, the ADE 415 can also be used in a modular fashion so that the user can use different modules individually and generate only partial reports.

As discussed above, the ADE 415 is configured to derive an optimized sustainable design for sensors and actuators including, for example, wearable sensors. Wearable sensors typically scavenge energy from light or human body heat. The availability of scavenging sources is unpredictable. Therefore, operation of such sensors must be optimized to achieve energy neutrality in order to ensure sustainable operation of the sensors. A system is energy neutral when the storage device level remains the same before and after a computation (i.e. energy needed for the computation is solely obtained from a scavenging source).

In this problem formulation, the ADE 415 optimizes the data sending frequency of the sensor depending on the availability of scavenging source. For example, if the sending frequency is $f_c$ when the scavenging source is available and $f_d$ when scavenging source is unavailable and, to achieve energy neutrality, the sensor battery is to be charged only when the scavenging source is available, the ADE 415 must find values of $f_c$ and $f_d$ such that the execution should require only the energy obtained from scavenged source. Further, even if the scavenging source is available, the sensor battery is unable to store energy beyond the battery capacity. Given these constraints, the ADE 415 will minimize $f_c$ and $f_d$. For problems like this, the ADE 415 may provide a set of time-constrained sustainable designs and the developer can choose a proposed design based on available sensors and their configuration settings.

Furthermore, as also noted above, the ADE 415 is configured to perform safety verification in the design of the smartphone MMA and the TDM. In some implementations, this is accomplished by implementing a theoretical safety verification to prove the design safety using model checking and reachability analysis techniques. The safety verification ensures that the side-effects of interactions between human physiology and sensors are within accepted limits. These interactions are typically governed by smartphone control algorithms when a sensor acts as an actuator. In such a scenario, the developer provides hybrid automata which is embedded in the control algorithm while specifying high-level design. Reachability analysis is then performed on the specified hybrid automata while considering optimized time constrained designs as an initial set.

In some implementations of the ADE 415, the safety verification methods use spatio-temporal hybrid automata (STHA) and a related reachability analysis algorithm. STHA considers the effect of interactions over time as well as over space to provide more accurate results as compared to only time-based analysis. Interactions are considered in the form of equation (1):

$$A_i \frac{\partial V}{\partial t} = B_i \frac{\partial^2 V}{\partial x^2} + C_i V + u_i \quad (1)$$

In some implementations, the ADE 415 allows the developer to specify requirements for various components such as sensing, computation, and communication. In sensing, the type of sensors, motes, sampling frequency, and sending frequency may be specified. The computation component may include processing of data on both sensors and smartphone which uses various physiological algorithms from a database including, for example, Fast Fourier Transform (FFT), peak detection, and mean. The developer can also add new algorithms as well as modify the inputs of existing available algorithms. Furthermore, as noted above, communication protocol between the sensors and the smartphone, as well as between the smartphone and the cloud, can be specified. The developer can also specify energy management techniques such as duty cycle and radio power level.

The ADE 415 can also provide the developer the ability to specify aspects of the security protocol selected from a security algorithm database (which can also be extended to include new security protocols as defined by a developer). As discussed above, the ADE 415 generates a TDM application, which ensures that wireless communication to and from the smartphone is secure. It includes a security algorithm specified by the developer and maintains a code template for generating the TDM application. The code for the specified security algorithm is accessed from a database and inserted into the code template. The code generator uses Application Programming Interfaces (APIs) to allow communication between external wireless mote and an smartphone, for example, via Bluetooth. The Bluetooth API ensures that a connection is established and that data communication between mote and smartphone while a sensor handler acts as a manager and registers all user assigned sensors, different algorithms associated with each sensor, and handling of data received from the particular sensor. For each of the wireless communication calls, the code generator of the ADE 415 appends the security protocol.

Lastly, the ADE 415 applies static analysis techniques to verify proper operation of the smartphone code and any code that will be run by an external sensor. The quality of application code may be quantified in terms of the number of defects found. The software generated by the ADE 415 may use a high-level language such as java, C#, or objective C. Although compilers for these languages may include advanced features to find bugs or errors in the code, the complexity involved in high-level languages, such as, for example, multithreading, methods, classes, and various design types, may make available compilers inefficient in identifying all bugs. Therefore, the ADE 415 also uses static analysis tools to make the resulting code more robust. Tools such as "Find Bugs" generate unit test cases, compute code metrics, and identify duplicate code, "dead code," misunderstood API methods, and other performance problems.

Thus, the invention provides, among other things, a combination of mobile medical applications running on a smartphone where all communications and data operations are handled by a separate data management application that is isolated from the code of the mobile medical applications and an automated development environment for assisting with the development of safety-verified code for the mobile medical applications and the separate data management application. Various features and advantages of the invention are set forth in the following claims.

What is claimed is:

1. A method of developing mobile medical software applications including a first mobile medical software application and a data manager software application, the method comprising:
receiving, by a code development system, specification information defining operational characteristics of the first mobile medical software application, the specification information including an identification of at least one external device;
automatically selecting, by the code development system based at least in part on the received specification information, portions of previously written software code stored on a non-transitory computer-readable memory of the code development system;
automatically generating, by the code development system, the data manager software application by arranging the selected portions of previously written software code based on the received specification information; and
generating the first mobile medical software application,
wherein the automatically generated data manager software application is configured to communicate with the first mobile medical software application and with the at least one external devices based on the received specification information, and
wherein the generated first mobile medical software application is configured to communicate with the at least one external device only through the data manager software application.

2. The method of claim 1, wherein the specification information includes an identification of an external medical sensor device from which the first mobile medical software application will receive patient data,
wherein automatically selecting, based on the received specification information, portions of previously written software code includes identifying a previously written sensor interface code segment of a plurality of previously written sensor interface code segments stored on the non-transitory computer-readable memory, the identified previously written sensor interface code being configured to provide for communication with the external sensor device identified by the specification information for the first mobile medical software application, and
wherein automatically generating the data manager software application includes accessing the identified previously written sensor interface code segment from the non-transitory computer-readable memory and including the previously written sensor interface code in the generated data manager software application.

3. The method of claim 1, wherein the specification information further includes data encryption requirements for communicating data between the first mobile medical software application and an external system,
wherein automatically selecting, based on the received specification information, portions of previously written software code includes identifying a previously written data encryption code segment of a plurality of previously written data encryption code segments stored on the non-transitory computer readable memory, the identified previously written data encryption code segment being configured to provide for encrypted data communication according to the data encryption requirements identified by the specification information for the first mobile medical software application, and
wherein automatically generating the data manager software application includes accessing the identified previously written data encryption code segment from the non-transitory computer-readable memory and including the previously written data encryption code segment in the generated data manager software application.

4. The method of claim 1, wherein the specification information includes an identification of a plurality of external devices with which the first mobile medical software application will exchange data, and wherein automatically generating the data manager software application includes:

running a multi-object optimization analysis to determine optimized communication specifications for concurrently communicating with the plurality of external devices, identifying, based on the multi-object optimization analysis, a subset of previously written code segments from a plurality of previously written code segments stored on the non-transitory computer-readable memory that together will satisfy communication requirements defined by the specification information for the first mobile medical software application, assembling the subset of previously written code segments and adjusting operating variables of the subset of previously written code segments to generate the data manager software application that is optimized for communicating with the specific plurality of external devices identified by the specification information for the first mobile medical software application.

5. The method of claim 1, wherein generating the first mobile medical software application includes:

automatically generating, by the code development system, a data communication code segment for the first mobile medical software application configured to provide for communication with the automatically generated data manager software application such that the first mobile medical software application will perform all data exchanges defined by the specification information with the automatically generated data manager software application; and including the automatically generated data communication code segment in the generated first mobile medical software application.

6. The method of claim 5, further comprising receiving, by the code development system, new source code for the first mobile medical software application, and wherein generating the first mobile medical software application includes integrating the new source code and the automatically generated data communication code segment into the first mobile medical software application.

7. The method of claim 6, wherein the new source code received by the code development system includes source code defining one or more data analysis operations to be performed by the first mobile medical software application.

8. The method of claim 6, wherein the new source code received by the code development system includes source code defining a graphical user interface to be displayed on a mobile device during operation of the first mobile medical software application.

9. The method of claim 1, further comprising receiving, by the code development system, new source code for the first mobile medical software application, and wherein generating the first mobile medical software application includes:

running a software optimization analysis on the new source code, modifying the new source code based on the software optimization analysis, and generating the first mobile medical software application based on the modified new source code.

10. The method of claim 1, wherein the previously written software code stored on the computer-readable memory has been previously reviewed and certified for use in medical software.

11. The method of claim 1, further comprising:

receiving, by the code development system, specification information for a second mobile medical software application, the specification information for the second mobile medical software application including an identification of at least one additional external device; and generating the second mobile medical software application wherein automatically selecting portions of previously written software code includes automatically identifying segments of previously written software code stored on the non-transitory computer-readable memory based on the specification information for the first mobile medical software application and the specification information for the second mobile medical software application, wherein automatically generating the data manager software application includes arranging the selected portions of previously written software code based on the specification information for the first mobile medical software application and the specification information for the second mobile medical software application, wherein the automatically generated data manager software application is configured to communicate with the first mobile medical software application, the second mobile medical software application, the at least one external device, and the at least one additional external device, and wherein the generated second mobile medical software application is configured to communicate with the at least one additional external device only through the data manager software application.

12. A mobile medical system comprising:

a first external medical device;

a second external medical device; and a mobile device including a processor and a non-transitory memory storing instructions that, when executed by the processor, operate a plurality of software applications including a first mobile medical software application, a second mobile medical software application, and a mobile medical data manager software application, wherein operating the mobile medical data manager includes providing all communication between the first mobile medical software application, the second mobile medical software application, the first external medical device, and the second external medical device, wherein operating the first mobile medical software application includes performing a first data operation related to a first medical function; and communicating with the mobile medical data manager to transfer data related to the first data operation to or from the first external medical device, wherein operating the second mobile medical software application includes performing a second data operation related to a second medical function, and communicating with the mobile medical data manger to transfer data related to the second data operation to or from the second external medical device, and wherein the first mobile medical software application and the second mobile medical software application do not communicate directly with any external device.

13. The mobile medical system of claim 12, wherein operating the first mobile medical software application includes communicating with the mobile medical data manager to transfer data related to the first data operation to or from the first external medical device and to or from the second external medical device.

14. The mobile medical system of claim 13, wherein the first external medical device includes a remote health record storage server and the second external medical device includes a medical sensor,
wherein operating the mobile medical data manager includes
receiving data from the medical sensor and providing the data from the medical sensor to the first mobile medical software application, and
receiving output data from the first mobile medical software application and transmitting the output data from the first mobile medical software application to the remote health record storage server, and
wherein operating the first mobile medical software application includes
receiving the medical sensor data from the mobile medical data manager,
performing the first data operation to process the medical sensor data and to generate the output data, and
providing the output data to the mobile medical data manager.

15. The mobile medical system of claim 14, wherein operating the second mobile medical software application includes
receiving the sensor data from the mobile medical data manager,
processing the sensor data, and
displaying information related to the sensor data on a display of the mobile device.

16. The mobile medical system of claim 12, wherein the first medical device includes a medical actuator device,
wherein operating the first mobile medical software application includes generating control data for the medical actuator device and providing the control data to the mobile medical data manager, and
wherein operating the mobile medical data manager includes receiving the control data from the first mobile medical software application and transmitting the control data to the medical actuator device.

17. The mobile medical system of claim 12, wherein the first medical device includes a remote storage server,
wherein operating the first mobile medical software application include providing data to be stored on the remote storage server to the mobile medical data manager, and
wherein operating the mobile medical data manager includes
receiving the data to be stored on the remote storage server from the first mobile medical software application,
encrypting the data to be stored on the remote storage server, and
transmitting the encrypted data to the remote storage server.

18. The mobile medical system of claim 13, wherein the mobile device is one selected from a group consisting of a smart phone and a tablet computer.

19. A code development system comprising:
a non-transitory computer-readable memory storing a plurality of previously written code segments;
a processor configured to
prevent a user from modifying the plurality of previously written code segments stored on the memory,
receive specification information from the user for a first mobile medical software application, wherein the specification information includes an identification of at least one external device,
automatically select, based at least in part on the received specification information, one or more code segments from the plurality of previously written code segments, the one or more code segments including a code segment for communicating with the at least one external device,
automatically generate a data manager software application by arranging the selecting one or more code segments based on the received specification information, and
generate the first mobile medical software application, wherein the first mobile medical software application is capable of communicating with the at least one external device only through the data manager software application.

* * * * *

UNITED STATES PATENT AND TRADEMARK OFFICE
CERTIFICATE OF CORRECTION

| | | |
|---|---|---|
| PATENT NO. | : 9,619,213 B2 | Page 1 of 1 |
| APPLICATION NO. | : 14/694152 | |
| DATED | : April 11, 2017 | |
| INVENTOR(S) | : Gupta et al. | |

It is certified that error appears in the above-identified patent and that said Letters Patent is hereby corrected as shown below:

On the Title Page

Item (72), add --Priyanka Bagade, Hillsboro, OR (US)--

Signed and Sealed this
Sixth Day of August, 2019

Andrei Iancu
*Director of the United States Patent and Trademark Office*